United States Patent
Bell et al.

(10) Patent No.: US 7,722,892 B2
(45) Date of Patent: May 25, 2010

(54) COMPOUNDS

(75) Inventors: Gordon Alastair Bell, Bracknell (GB);
Clifford Arthur Hart, Bracknell (GB);
Roger Cyril Murfitt, Bracknell (GB);
Peter Bernard Sutton, Bracknell (GB)

(73) Assignee: Syngenta Crop Protection, Inc., Greensboro, NC (US)

( * ) Notice: Subject to any disclaimer, the term of this patent is extended or adjusted under 35 U.S.C. 154(b) by 1569 days.

(21) Appl. No.: 10/488,564

(22) PCT Filed: Aug. 23, 2002

(86) PCT No.: PCT/GB02/03906

§ 371 (c)(1),
(2), (4) Date: Oct. 21, 2004

(87) PCT Pub. No.: WO03/022048

PCT Pub. Date: Mar. 20, 2003

(65) Prior Publication Data

US 2005/0054538 A1    Mar. 10, 2005

(30) Foreign Application Priority Data

Sep. 6, 2001    (GB) ............... 0121580.5

(51) Int. Cl.
*A01N 25/02* (2006.01)
*A01N 25/30* (2006.01)
(52) U.S. Cl. .................. 424/405; 504/118
(58) Field of Classification Search ........... 424/405; 514/785; 504/118
See application file for complete search history.

(56) References Cited

U.S. PATENT DOCUMENTS

| 4,215,116 | A | 7/1980 | Lover et al. |
| 4,938,797 | A | 7/1990 | Hässlin et al. |
| 5,393,791 | A | 2/1995 | Roberts |
| 5,580,567 | A | 12/1996 | Roberts |
| 6,068,849 | A | 5/2000 | Garst et al. |
| 6,235,300 | B1 * | 5/2001 | Brumbaugh ........... 424/405 |

FOREIGN PATENT DOCUMENTS

| EP | 0968649 | 5/2000 |
| WO | WO9518531 | 7/1995 |
| WO | 9835553 | 8/1998 |
| WO | WO9903343 | 1/1999 |
| WO | 9926472 | 3/1999 |

* cited by examiner

*Primary Examiner*—Joseph K. McKane
*Assistant Examiner*—Janet L Coppins
(74) *Attorney, Agent, or Firm*—William A. Teoli, Jr.

(57) ABSTRACT

An adjuvant suitable for use with a lipophilic agrochemical has the formula (I), $R_1-(CO)_m-O-[-R_2O-]_n-R_3$, wherein $R_1$ is a $C_{16}$ to $C_{20}$ straight or branched chain alkyl or alkenyl group, $R_2$ is ethyl or isopropyl, n is from 8 to 30 and m is 0 or 1 and when $R_2$ is ethyl, $R_3$ is a $C_1$ to $C_7$ alkyl group and when $R_2$ is isopropyl, $R_3$ is hydrogen or a $C_1$ to $C_7$ alkyl group, provided that when $R_1$ is oleyl, $R_2$ is isopropyl and $R_3$ is hydrogen, n is not 10. An adjuvant composition comprising an agrochemical and an adjuvant of formula (I) is also claimed. Adjuvants of the invention show effective bioperformance enhancement despite having little or no surfactant properties.

10 Claims, No Drawings

COMPOUNDS

This application is a 371 of International Application No. PCT/GB02/03906 filed Aug. 23, 2002, which claims priority to GB 0121580.5, filed Sep. 6, 2001, the contents of which are incorporated herein by reference.

This invention relates to novel compounds and in particular to novel adjuvants and to their use in agrochemical formulations.

A wide variety of adjuvants are available to those skilled in the art for the improvement of the bioperformance of active ingredients such as agrochemicals. In addition to the effect on bioperformance, the physical properties of an adjuvant are of key importance and must be selected with a view to compatibility with the formulation concerned. Thus by way of a single example, it is generally simpler to incorporate a solid adjuvant into a solid formulation such as a water-soluble or water-dispersible granule. In general adjuvants rely on surfactant properties for bioperformance enhancement and one typical class of adjuvants involves an alkyl or aryl group to provide a lipophilic moiety and a (poly)ethoxy chain to provide a hydrophilic moiety. Much has been published on the selection of adjuvants for various purposes and in Hess, F. D. and Foy, C. L., Weed technology, 2000, 14, 807-813 for example it is disclosed that adjuvants for use with lipophilic agrochemical active ingredients are generally of relatively low molecular weight with a degree of ethoxylation which leads to a hydrophile lipophile balance (HLB) of 8 or less. This corresponds to a surfactant with 12 carbon atoms in the lipophilic chain and between 2 and 3 moles of ethoxylate in the hydrophilic portion of the adjuvant. Similarly a surfactant with a longer carbon chain, such as 18 atoms, would have four or less moles of ethoxylate.

Propoxylate groups are considered to be lipophilic. A molecule with a hydrocarbon chain and propoxylate groups would not be considered to have an BLB value and would normally not be considered as a surfactant.

Particular care is required when selecting bioperformance enhancing adjuvants for incorporation in a microencapsulated presentation of an active ingredient, since many conventional ethoxylated adjuvants interfere with the microcapsule wall-forming reaction at the oil/water interface. Use of such adjuvants results in weak or ruptured microcapsules and their presence is therefore undesirable.

In GB 2024626 there is disclosed a range of polypropylene glycol derivatives suitable for destroying mites or ectoparasites and their eggs. In Table 3 there is disclosed propoxylated (10) oleyl alcohol.

We have now found that certain novel alkoxylated long-chain alcohols and acids and end-capped variants thereof, despite having little or no surfactant properties, are unexpectedly effective bioperformance enhancing adjuvants and furthermore have physical properties and attributes that render then particularly effective in certain formulation vehicles.

According to the present invention there is provided an adjuvant having the formula (I)

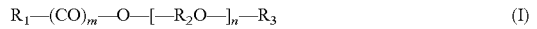
(I)

wherein $R_1$ is a $C_{16}$ to $C_{20}$ straight or branched chain alkyl or alkenyl group, $R_2$ is ethyl or isopropyl, n is from 8 to 30 and m is 0 or 1 and when $R_2$ is ethyl, $R_3$ is a $C_1$ to $C_7$ alkyl group and when $R_2$ is isopropyl, $R_3$ is hydrogen or a $C_1$ to $C_7$ alkyl group, provided that when $R_1$ is oleyl, $R_2$ is isopropyl and $R_3$ is hydrogen, n is not 10.

According to a further aspect of the present invention there is provided an agrochemical composition comprising a herbicide or fungicide and an adjuvant having the formula (I)

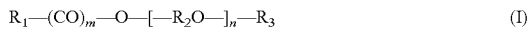
(I)

wherein $R_1$ is a $C_{16}$ to $C_{20}$ straight or branched chain alkyl or alkenyl group, $R_2$ is ethyl or isopropyl, n is from 8 to 30 and m is 0 or 1 and when $R_2$ is ethyl, $R_3$ is a $C_1$ to $C_7$ alkyl group and when $R_2$ is isopropyl, $R_3$ is hydrogen or a $C_1$ to $C_7$ alkyl group.

The agrochemical is preferably a lipophilic herbicide or fungicide.

When $R_1$ is an alkenyl group it may have one or more double bonds which may be in either cis or trans configuration(s). Preferably $R_1$ has from 1 to 3 double bonds. It is generally preferred that the double bond(s) are in the cis configuration. It is especially preferred that $R_1$ is a $C_{18}$ branched chain alkyl or $C_{18}$ alkenyl group for example oleyl or isostearyl (derived from the alcohol, 2-hexyl-dodecan-1-ol).

The value of n is preferably from 10 to 30 and especially from 10 to 20. The value of n may be an integer when a specific and uniform number of groups $R_2O$ are introduced or may be an average value when a range of numbers of such groups are introduced.

The value of m is preferably 0.

When $R_3$ is not hydrogen it is preferably a $C_1$ to $C_4$ alkyl group and in particular methyl or butyl. Butyl is especially preferred. Those skilled in the art will appreciate that an alkyl group $R_3$ represents an "end cap" to the terminal hydroxyl of the group

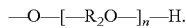

Since "end capping" a terminal ethylene oxide group ($R_2$ is ethyl) removes certain undesirable properties (such as the interference with the microencapsulation process) as discussed herein, it is desirable in order to achieve the objects of the invention to "end cap" substantially all of the terminal hydroxyl groups when $R_2$ is ethyl. Thus $R_3$ is not hydrogen when $R_2$ is ethyl. When $R_2$ is isopropyl on the other hand, $R_3$ may be hydrogen or alkyl since both moieties achieve the objects of the invention. It is thus possible to "end cap" only a proportion of the terminal hydroxyl groups such that $R_3$ is a mixture of hydrogen and alkyl groups.

We have found that both propoxylated oleyl and isostearyl alcohols (when the value of m is 0) and acids (when the value of m is 1) and their end-capped equivalents show no significant surfactant properties. These materials do not contain a hydrophilic moiety and would not be considered to have an HLB classification. Attempts to use these materials to emulsify a simple oil such as decane into water showed that separation into two phases occurred even after vigorous shaking. Where some small amount of emulsification was observed this was found to be short lived. Surprisingly the bioperformance enhancement, in particular for lipophilic agrochemicals, is excellent despite the lack of surfactant properties. Moreover, the absence of surfactant properties may bring a number of advantages such as reduced spray drift, a reduction in adverse interaction with surfactants added for formulation purposes (such as suspension of a dispersed solid) and reduced gelling of the formulation. Moreover the adjuvants are generally liquids (oils) which are substantially insoluble in water and are readily compatible for example with emulsion concentrates in which they dissolve in the oil phase. They are also more readily used as stand-alone tank mix adjuvants since they are oil-soluble. Increasing the molecular weight, for example using butyl end-capping and a value of n towards the upper end of the range, may produce a solid adjuvant which is for example well adapted for incorporation in solid formulations such as water-soluble or water-dispersible granules. In general the propoxylated adjuvants of the present invention are liquid whereas the ethoxylates are either solid or semi-solid. An exception is oleyl 10 EO with a butyl end cap which is a liquid.

We have found similarly that ethoxylated oleyl and isostearyl end-capped methyl and butyl ethers show no significant surfactant properties. They generally have different physical properties from the uncapped equivalents which can be used to advantage. For example oleyl 10 EO end-capped butyl ether is an oily liquid which emulsifies readily in water whilst the uncapped oleyl 10 EO equivalent forms viscous liquid crystals on contact with water. Increasing the molecular weight, for example using butyl end-capping and a value of n towards the upper end of the range, may produce a solid adjuvant which is for example well adapted for incorporation in solid formulations such as water-soluble or water-dispersible granules. Typical of such a solid adjuvant according to the present invention is oleyl 20 EO end-capped with butyl (i.e. the compound in which $R_1$ is oleyl, $R_2$ is ethyl, n is 20 and $R_3$ is butyl).

As specific examples of the adjuvants of the present invention or which may be used in agrochemcial compositions of the present invention there may be mentioned oleyl 10 propylene oxide (i.e. a compound of Formula (1) wherein R1 is oleyl, m is 0, $R_2$ is isopropylene, n is 10 and $R_3$ is hydrogen), oleyl 10 propylene oxide end-capped butyl ether (i.e. a compound of Formula (1) wherein $R_1$ is oleyl, m is 0, $R_2$ is isopropylene, n is 10 and $R_3$ is butyl), oleyl 20 propylene oxide, oleyl 20 propylene oxide end-capped butyl ether, isostearyl 10 propylene oxide, isostearyl 20 propylene oxide, oleyl 10 ethylene oxide end-capped butyl ether, oleyl 20 ethylene oxide end-capped butyl ether, oleic acid 10 ethylene oxide end-capped methyl ether (i.e. a compound of Formula (1) wherein R1 is oleyl, m is 1, $R_2$ is ethylene, n is 10 and $R_3$ is methyl), oleic acid 20 ethylene oxide end-capped methyl ether.

Adjuvants of the present invention are generally compatible with microencapsulation processes and can be incorporated as bioperformance enhancing adjuvant in a microencapsulated agrochemical formulation without detriment to the microcapsule properties. In contrast conventional ethoxylated alcohol surfactants tend to interfere with interfacial polymerisation wall-forming processes which are key to most conventional microencapsulation processes.

Adjuvants of the present invention have a variety of uses but are particularly suitable for enhancing the bioperformance of lipophilic agrochemicals, including herbicides, fungicides and insecticides. Examples of suitable lyophilic agrochemicals include herbicides such as fluzifop, mesotrione, fomesafen, tralkoxydim, napropamide, amitraz, propanil, cyprodanil, pyrimethanil, dicloran, tecnazene, toclofos methyl, flamprop M, 2,4-D, MCPA, mecoprop, clodinafop-propargyl, cyhalofop-butyl, diclofop methyl, haloxyfop, quizalofop-P, indol-3-ylacetic acid, 1-naphthylacetic acid, isoxaben, tebutam, chlorthal dimethyl, benomyl, benfuresate, dicamba, dichlobenil, benazolin, triazoxide, fluazuron, teflubenzuron, phenmedipham, acetochlor, alachlor, metolachlor, pretilachlor, thenylchlor, alloxydim, butroxydim, clethodim, cycloxydim, sethoxydim, tepraloxydim, pendimethalin, dinoterb, bifenox, oxyfluorfen, acifluorfen, fluoroglycofen-ethyl, bromoxynil, ioxynil, imazamethabenz-methyl, imazapyr, imazaquin, imazethapyr, imazapic, imazamox, flumioxazin, flumiclorac-pentyl, picloram, amodosulfuron, chlorsulfuron, nicosulfuron, rimsulfuron, triasulfuron, triallate, pebulate, prosulfocarb, molinate, atrazine, simazine, cyanazine, ametryn, prometryn, terbuthylazine, terbutryn, sulcotrione, isoproturon, linuron, fenuron, chlorotoluron, metoxuron, 8-(2,6-diethyl-4-methyl-phenyl)tetrahydropyrazolo[1,2-d][1,4,5]oxadiazepine-7,9-dione and 2,2,-dimethyl-propionic acid-8-(2,6-diethyl-4-methyl-phenyl)-9-oxo-1,2,4,5-tetrahydro-9H-pyrazolo[1,2-d][1,4,5] oxadiazepine-7-yl ester, fungicides such as azoxystrobin, trifloxystrobin, kresoxim methyl, famoxadone, metominostrobin, picoxystrobin, dimoxystrobin, fluoxastrobin, orysastrobin, metominostrobin, prothioconazole, carbendazim, thiabendazole, dimethomorph, vinclozolin, iprodione, dithiocarbamate, imazalil, prochloraz, fluquinconazole, epoxiconazole, flutriafol, azaconazole, bitertanol, bromuconazole, cyproconazole, difenoconazole, hexaconazole, paclobutrazole, propiconazole, tebuconazole, triadimefon, trtiticonazole, fenpropimorph, tridemorph, fenpropidin, mancozeb, metiram, chlorothalonil, thiram, ziram, captafol, captan, folpet, fluazinam, flutolanil, carboxin, metalaxyl, bupirimate, ethirimol, and insecticides such as thiamethoxam, imidacloprid, acetamiprid, clothianidin, dinotefuran, nitenpyram, fipronil, abamectin, emamectin, bendiocarb, carbaryl, fenoxycarb, isoprocarb, pirimicarb, propoxur, xylylcarb, asulam, chlorpropham, endosulfan, heptachlor, tebufenozide, bensultap, diethofencarb, pirimniphos methyl, aldicarb, methomyl, cyprmethrin, bioallethrin, deltamethrin, lambda cyhalothrin, cyhalothrin, cyfluthrin, fenvalerate, imiprothrin, permetlrin, halfenprox.

Adjuvants of the present invention may be prepared by conventional techniques. Thus for example the ethoxylated or propopoxylated alcohol or acid may be manufactured by base catalysed condensation of the relevant alcohol or acid (for example oleyl or isostearyl alcohol or acid) with ethylene oxide (or propylene oxide as the case may be). End-capped derivatives may be obtained by reacting the ethoxylated or propoxylated alcohol or acid with the appropriate alkyl halide (for example butyl chloride) in the presence of a base.

The proportion of adjuvant relative to active ingredient can readily be selected by one skilled in the art to meet the intended utility. Typically the ratio of adjuvant to active ingredient will range from 1:50 and 200:1 and preferably from 1:5 to 20:1

The invention is illustrated by the following Examples in which all parts and percentages are by weight unless otherwise stated.

EXAMPLES 1 TO 10

Compounds of the present invention or for use in agrochemical compositions of the present invention are characterised as indicated below. In each case NMR spectra were run as 10% v/v solutions in CDCl3 on a Varian Inova 400 spectrometer. A bold and underlined hydrogen indicates the hydrogen responsible for the relevant signal.

Oleyl 10 Propylene Oxide

| | | | | |
|---|---|---|---|---|
| δ5.34 | multiplet | | 2H | oleyl 9 & 10CH |
| δ4-3 | multiplet | | 32H | oleyl 1CH$_2$ & propoxyl 1CH$_2$ & 2CH |
| δ2.01 | multiplet | | 4H | oleyl 8 & 11CH$_2$ |
| δ1.56 | multiplet | | 2H | oleyl 2CH$_2$ |
| δ1.26 | mutliplet | | 22H | oleyl 3-7 & 12-17CH$_2$ |
| δ1.14 | multiplet | | 30H | propoxylate 3CH$_3$ |
| δ0.88 | triplet | J ≈ 6.9 Hz | 3H | oleyl 18CH$_3$ |

Oleyl 10 Propylene Oxide End-Capped butyl ether

| | | | | |
|---|---|---|---|---|
| δ5.34 | multiplet | | 2H | oleyl 9 & 10CH |
| δ4-3 | multiplet | | 34H | butyl 1CH$_2$, oleyl 1CH$_2$ & propoxyl 1CH$_2$ & 2CH |
| δ2.02 | multiplet | | 4H | oleyl 8 & 11CH$_2$ |
| δ1.55 | multiplet | | 4H | oleyl 2CH$_2$ & butyl 2CH$_2$ |
| δ1.35 | sextuplet | | 2H | butyl 3CH$_2$ |
| δ1.26 | mutliplet | | 22H | oleyl 3-7 & 12-17CH$_2$ |
| δ1.14 | multiplet | | 30H | propoxylate 3CH$_3$ |
| δ0.92 | triplet | J ≈ 7.3 Hz | 3H | butyl 4CH$_3$ |
| δ0.88 | triplet | J ≈ 7.0 Hz | 3H | oleyl 18CH$_3$ |

Oleyl 20 Propylene Oxide

| | | | | |
|---|---|---|---|---|
| δ5.34 | multiplet | | 2H | oleyl 9 & 10CH |
| δ4-3 | multiplet | | 62H | oleyl 1CH$_2$ & propoxyl 1CH$_2$ & 2CH |
| δ2.01 | multiplet | | 4H | oleyl 8 & 11CH$_2$ |
| δ1.56 | multiplet | | 2H | oleyl 2CH$_2$ |
| δ1.26 | mutliplet | | 22H | oleyl 3-7 & 12-17CH$_2$ |
| δ1.14 | multiplet | | 60H | propoxylate 3CH$_3$ |
| δ0.88 | triplet | J ≈ 6.9 Hz | 3H | oleyl 18CH$_3$ |

Oleyl 20 Propylene Oxide End-Capped butyl ether

| | | | | |
|---|---|---|---|---|
| δ5.34 | multiplet | | 2H | oleyl 9 & 10CH |
| δ4-3 | multiplet | | 64H | butyl 1CH$_2$, oleyl 1CH$_2$ & propoxyl 1CH$_2$ & 2CH |
| δ2.02 | multiplet | | 4H | oleyl 8 & 11CH$_2$ |
| δ1.55 | multiplet | | 4H | oleyl 2CH$_2$ & butyl 2CH$_2$ |
| δ1.35 | sextuplet | | 2H | butyl 3CH$_2$ |
| δ1.26 | mutliplet | | 22H | oleyl 3-7 & 12-17CH$_2$ |
| δ1.14 | multiplet | | 60H | propoxylate 3CH$_3$ |
| δ0.92 | triplet | J ≈ 7.3 Hz | 3H | butyl 4CH$_3$ |
| δ0.88 | triplet | J ≈ 7.0 Hz | 3H | oleyl 18CH$_3$ |

Isostearyl (2-hexyl-dodecan-1-ol) 10 Propylene Oxide

| | | | | |
|---|---|---|---|---|
| δ4-3 | multiplet | | 32H | dodecyl 1CH$_2$ & propoxyl 1CH$_2$ & 2CH |
| δ1.56 | multiplet | | 2H | dodecyl 2CH$_2$ |
| δ1.26 | mutliplet | | 27H | dodecyl 3-11CH$_2$, 6CH & hexyl 1-5CH$_2$ |
| δ1.14 | multiplet | | 30H | propoxylate 3CH$_3$ |
| δ0.88 | triplet | J ≈ 6.9 Hz | 3H | decyl 12CH$_3$ & hexyl 6CH$_3$ |

Isostearyl (2-hexyl-dodecan-1-ol) 20 Propylene Oxide

| | | | | |
|---|---|---|---|---|
| δ4-3 | multiplet | | 62H | dodecyl 1CH$_2$ & propoxyl 1CH$_2$ & 2CH |
| δ1.56 | multiplet | | 2H | dodecyl 2CH$_2$ |
| δ1.26 | mutliplet | | 27H | dodecyl 3-11CH$_2$, 6CH & hexyl 1-5CH$_2$ |
| δ1.14 | multiplet | | 60H | propoxylate 3CH$_3$ |
| δ0.88 | triplet | J ≈ 6.9 Hz | 3H | decyl 12CH$_3$ & hexyl 6CH$_3$ |

Oleyl 10 Ethylene Oxide End-Capped Butyl Ether

| | | | | |
|---|---|---|---|---|
| δ5.35 | multiplet | | 2H | oleyl 9 & 10CH |
| δ3.65 | singlet | | 32H | polyethoxyl mid chain CH$_2$ |
| δ3.63 | multiplet | | 4H | polyethoxyl —OCH$_2$CH$_2$OR |
| δ3.58 | multiplet | | 4H | polyethoxyl —OCH$_2$CH$_2$OR |
| δ3.46 | triplet | J ≈ 6.5 Hz | 2H | butyl 1CH$_2$ |
| δ3.46 | triplet | J ≈ 6.5 Hz | 2H | oleyl 1CH$_2$ |
| δ2.01 | multiplet | | 4H | oleyl 8 & 11CH$_2$ |
| δ1.57 | multiplet | | 4H | oleyl 2CH$_2$ & butyl 2CH$_2$ |
| δ1.35 | sextuplet | | 2H | butyl 3CH$_2$ |
| δ1.26 | mutliplet | | 22H | oleyl 3-7 & 12-17CH$_2$ |
| δ0.92 | triplet | J ≈ 7.3 Hz | 3H | butyl 4CH$_3$ |
| δ0.88 | triplet | J ≈ 7.0 Hz | 3H | oleyl 18CH$_3$ |

Oleyl 20 Ethylene Oxide End-Capped Butyl Ether

| | | | | |
|---|---|---|---|---|
| δ5.35 | multiplet | | 2H | oleyl 9 & 10CH |
| δ3.65 | singlet | | 72H | polyethoxyl mid chain CH$_2$ |
| δ3.63 | multiplet | | 4H | polyethoxyl —OCH$_2$CH$_2$OR |
| δ3.58 | multiplet | | 4H | polyethoxyl —OCH$_2$CH$_2$OR |
| δ3.46 | triplet | J ≈ 6.5 Hz | 2H | butyl 1CH$_2$ |
| δ3.46 | triplet | J ≈ 6.5 Hz | 2H | oleyl 1CH$_2$ |
| δ2.01 | multiplet | | 4H | oleyl 8 & 11CH$_2$ |
| δ1.57 | multiplet | | 4H | oleyl 2CH$_2$ & butyl 2CH$_2$ |
| δ1.35 | sextuplet | | 2H | butyl 3CH$_2$ |
| δ1.26 | mutliplet | | 22H | oleyl 3-7 & 12-17CH$_2$ |
| δ0.92 | triplet | J ≈ 7.3 Hz | 3H | butyl 4CH$_3$ |
| δ0.88 | triplet | J ≈ 7.0 Hz | 3H | oleyl 18CH$_3$ |

Oleic Acid 10 Ethylene Oxide End-Capped Methyl Ether

| | | | | |
|---|---|---|---|---|
| δ5.33 | multiplet | | 2H | oleoyl 9 & 10CH |
| δ4.22 | triplet | J ≈ 4.9 Hz | 2H | polyethoxyl —OCH$_2$CH$_2$OC=O |
| δ3.70 | triplet | J ≈ 4.9 Hz | 2H | polyethoxyl —OCH$_2$CH$_2$OC=O |
| δ3.65 | singlet | | 34H | polyethoxyl mid chain CH$_2$ |
| δ3.55 | triplet | J ≈ 4.9 Hz | 2H | polyethoxyl —OCH$_2$CH$_2$OCH$_3$ |
| δ3.38 | singlet | | 2H | —OCH$_3$ |
| δ2.33 | triplet | J ≈ 7.5 Hz | 2H | oleoyl 2CH$_2$ |
| δ2.01 | multiplet | | 4H | oleoyl 8 & 11CH$_2$ |
| δ1.62 | multiplet | | 2H | oleyl 3CH$_2$ |
| δ1.28 | mutliplet | | 20H | oleyl 4-7 & 12-17CH$_2$ |
| δ0.88 | triplet | J ≈ 7.0 Hz | 3H | oleyl 18CH$_3$ |

Oleic Acid 20 Ethylene Oxide End-Capped Methyl Ether

| | | | | |
|---|---|---|---|---|
| δ5.33 | multiplet | | 2H | oleoyl 9 & 10CH |
| δ4.22 | triplet | J ≈ 4.9 Hz | 2H | polyethoxyl —OCH$_2$CH$_2$OC=O |
| δ3.70 | triplet | J ≈ 4.9 Hz | 2H | polyethoxyl —OCH$_2$CH$_2$OC=O |
| δ3.65 | singlet | | 74H | polyethoxyl mid chain CH$_2$ |
| δ3.55 | triplet | J ≈ 4.9 Hz | 2H | polyethoxyl —OCH$_2$CH$_2$OCH$_3$ |
| δ3.38 | singlet | | 2H | —OCH$_3$ |
| δ2.33 | triplet | J ≈ 7.5 Hz | 2H | oleoyl 2CH$_2$ |
| δ2.01 | multiplet | | 4H | oleoyl 8 & 11CH$_2$ |
| δ1.62 | multiplet | | 2H | oleyl 3CH$_2$ |
| δ1.28 | mutliplet | | 20H | oleyl 4-7 & 12-17CH$_2$ |
| δ0.88 | triplet | J ≈ 7.0 Hz | 3H | oleyl 18CH$_3$ |

EXAMPLES 11 TO 14

An agrochemical composition was prepared containing 0.2% v/v of an adjuvant in a track sprayer containing fluazifop P butyl emulsified at one of four different concentrations. Weeds which had been grown to the 2.3 leaf stage were sprayed using volumes of 200 l/ha. Each sample was replicated three times. The following weed species were tested:—

AVEFA *Avena fatua* (wild oats)
LOLRI *Lolium rigidum* (rye grass)
TRZAW *Triticum aestivum* (wheat)
SETVI *Setaria viridis* (green foxtails)

Activity was measured 21 days after treatment and was compared with a standard composition containing only fluazifop-p-butyl. The concentration required to provide 90% weed kill was calculated and is given in TABLE 1 below together with the mean ED90 across the species.

TABLE 1

ED90 Values (g/ha) for Adjuvants of the Invention with Fluazifop-p-butyl

| Adjuvant | AVEFA | LOLRI | TRZAW | SETVI | Mean (g/ha) |
|---|---|---|---|---|---|
| Oleyl 20E Bu Ether | 19.5 | 27.5 | 21.4 | 16.5 | 21.2 |
| Oleic 10E Me Ether | 16.7 | 34.8 | 28.4 | 15.8 | 23.9 |
| Oleyl 10P Bu Ether | 19.8 | 34.9 | 29.2 | 16.7 | 25.2 |
| Oleyl 20P Bu Ether | 23.4 | 48.6 | 32.2 | 19 | 30.8 |
| No Adjuvant | 36.7 | 81.9 | 66.6 | 45.8 | 57.8 |

EXAMPLES 15 TO 25

Further adjuvants of the present invention were tested for activity in combination with fluzifop-p-butyl. Activity (% weed kill) was measured 21 days after treatment and is given as a mean of 3 replicates and 4 rates of fluazifop-p-butyl. All adjuvants were applied at 0.2% v/v. The results are given in Table 2 in comparison with a corresponding composition containing no adjuvant.

TABLE 2

Mean Activity (%)

| Adjuvant | TRZAW | SETVI | LOLRI | AVEFA | Mean over all species |
|---|---|---|---|---|---|
| No adjuvant | 19.3 | 58.2 | 37.1 | 62.4 | 44 |
| Isostearyl 20 PO | 37.3 | 80.9 | 52.5 | 58 | 57 |
| Oleyl 20 PO Bu ether | 38.8 | 75.9 | 46 | 67.4 | 57 |
| Oleyl 20 PO | 53.3 | 80.4 | 36.3 | 70.6 | 60 |
| Oleyl 20 EO Me ether | 52.1 | 74.6 | 54.9 | 72.3 | 63 |
| Isostearyl 10 PO | 53.8 | 81.8 | 51.8 | 67.8 | 64 |
| Oleyl 10 PO Bu ether | 45.8 | 84.2 | 54.4 | 71.4 | 64 |
| Oleyl 10 EO Me ether | 56.1 | 78.4 | 56.2 | 71.3 | 66 |
| Oleyl 10PO | 54.3 | 84.6 | 55.9 | 72.6 | 67 |
| Oleyl 10 EO Bu ether | 56 | 85.6 | 56.5 | 73.3 | 68 |
| Oleyl 20 EO Bu ether | 59.3 | 78.1 | 68.8 | 76.1 | 71 |

EXAMPLES 26 AND 27

The indicated adjuvants were evaluated in combination with a thin leaved grass herbicide 2,2,-dimethyl-propionic acid-8-(2,6-diethyl-4-methyl-phenyl)-9-oxo-1,2,4,5-tetrahydro-9H-pyrazolo[1,2-d][1,4,5]oxadiazepine-7-yl ester. The weeds were sprayed at the growth stages shown in the table with pesticide emulsions using a track sprayer and volumes of 200 l/ha. The adjuvants were added at 5% v/v as tank mix additives. Each result is the average of two replicates.

| Treatment | Rate gai/ha | ALOMY | APESV | AVEFA | LOLMU | PHAPA | Mean All Weeds |
|---|---|---|---|---|---|---|---|
| No Adjuvant | 5 | 5 | 5 | 0 | 0 | 0 | 2 |
|  | 7.5 | 13 | 5 | 0 | 0 | 5 | 5 |
|  | 10 | 23 | 3 | 0 | 25 | 3 | 11 |
| 0.5% Oleyl 10PO | 5 | 55 | 23 | 70 | 33 | 23 | 41 |
|  | 7.5 | 70 | 89 | 96 | 60 | 98 | 83 |
|  | 10 | 92 | 98 | 98 | 80 | 99 | 93 |
| 0.5% Oleyl 10EO butyl capped | 5 | 53 | 53 | 89 | 91 | 93 | 76 |
|  | 7.5 | 75 | 97 | 98 | 98 | 96 | 93 |
|  | 10 | 88 | 98 | 99 | 93 | 99 | 95 |

APESV (*Apera Spica-Venti*)
PHAPA (*Phalaris paradoxa*)

EXAMPLE 28

This example demonstrates the improvement in the biological activity of the fungicide azoxystrobin when applied with one of the novel adjuvants in glasshouse tests. The results quoted are the mean percentage disease control from four replicates on barley inoculated with *Puccinia recondita*. Azoxystrobin was applied from the commercial formulation Quadris 25 SC which was diluted to the strengths shown in the table. The adjuvant was added as a 0.5% v/v tank mix.

| Azoxystrobin mgai/l | No adjuvant control | Oleyl 20E Butyl capped |
|---|---|---|
| 2.5 | 10.5 | 90.5 |
| 1.25 | 1.8 | 82.7 |
| 0.625 | 2.3 | 66.5 |
| 0 | 0 | 5.9 |

The invention claimed is:

1. An adjuvant having the formula (I)

$$R_1-(CO)_m-O-[-R_2O-]_n-R_3 \quad (I)$$

wherein $R_1$ is oleyl or isostearyl, $R_2$ is ethylene or isopropylene, n is from 8 to 30 and m is 0 and when $R_2$ is ethylene, $R_3$ is a $C_1$ to $C_7$ alkyl group, and when $R_2$ is isopropylene, $R_3$ is hydrogen or a $C_1$ to $C_7$ alkyl group, provided that when $R_1$ is oleyl, $R_2$ is isopropylene and $R_3$ is hydrogen, n is not 10.

2. An adjuvant according to claim 1 wherein n is from 10 to 20.

3. An adjuvant according to claim 1 wherein when $R_3$ is not hydrogen it is methyl or butyl.

4. Oleyl 10 propylene oxide end-capped butyl ether, oleyl 20 propylene oxide, oleyl 20 propylene oxide end-capped butyl ether, isostearyl 10 propylene oxide, isostearyl 20 propylene oxide, 10 ethylene oxide end-capped butyl ether, oleyl 20 ethylene oxide end-capped butyl ether, oleic acid 10 ethylene oxide end-capped methyl ether, and oleic acid 20 ethylene oxide end-capped methyl ether.

5. An agrochemical composition comprising an adjuvant according to claim 4.

6. An agrochemical composition being encapsulated in a microcapsule and comprising a herbicide or fungicide and an adjuvant having the formula (I)

$$R_1-(CO)_m-O-[-R_2O-]_n-R_3 \quad (I)$$

wherein $R_1$ is a $C_{16}$ to $C_{20}$ straight or branched chain alkyl or alkenyl group, $R_2$ is ethyl or isopropyl, n is from 8 to 30 and m is 0 or 1 and when $R_2$ is ethyl, $R_3$ is a $C_1$ to $C_7$ alkyl group and when $R_2$ is isopropyl, $R_3$ is hydrogen or a $C_1$ to $C_7$ alkyl group.

7. An agrochemical composition according to claim 6 wherein the agrochemical is fluazifop-p-butyl, azoxystrobin or 2,2,-dimethyl-propionic acid-8-(2,6-diethyl-4-methyl-phenyl)-9-oxo-1,2,4,5-tetrahydro-9H-pyrazolo[1,2-d][1,4,5]oxadiazepine-7-yl ester.

8. An adjuvant according to claim 1 wherein $R_1$ is oleyl, $R_2$ is ethyl, $R_3$ is butyl, n is 20, and m is 0.

9. An agrochemical composition according to claim 6 wherein the agrochemical is azoxystrobin.

10. An agrochemical composition according to claim 6 wherein the agrochemical is azoxystrobin and the adjuvant is oleyl 20 ethylene oxide end-capped butyl ether.

* * * * *